US007094213B1

(12) United States Patent
Cook

(10) Patent No.: US 7,094,213 B1
(45) Date of Patent: Aug. 22, 2006

(54) ADJUSTABLE FOOT AND ANKLE DEVICE FOR GAIT CONTROL

(76) Inventor: Gerry Cook, 3115 N. Boyer Ave., Sandpoint, ID (US) 83864

( * ) Notice: Subject to any disclaimer, the term of this patent is extended or adjusted under 35 U.S.C. 154(b) by 76 days.

(21) Appl. No.: 10/821,378

(22) Filed: Apr. 9, 2004

Related U.S. Application Data

(60) Provisional application No. 60/462,413, filed on Apr. 10, 2003.

(51) Int. Cl.
*A61F 13/06* (2006.01)
(52) U.S. Cl. .............................. 602/65; 602/27; 602/23; 36/140
(58) Field of Classification Search .................. 602/23, 602/27–28, 65, 29, 5, 24, 60–63; 36/140, 36/88, 89, 115; 128/869, 882
See application file for complete search history.

(56) References Cited

U.S. PATENT DOCUMENTS

| 892,152 | A | * | 6/1908 | Harman ....................... 36/72 R |
|---|---|---|---|---|
| 3,976,059 | A | | 8/1976 | Lonardo |
| 4,392,487 | A | | 7/1983 | Selner et al. |
| 4,729,370 | A | | 3/1988 | Kallassy |
| 4,753,228 | A | | 6/1988 | Selner et al. |
| 5,067,486 | A | | 11/1991 | Hely |
| 5,298,013 | A | | 3/1994 | Lonardo |
| 5,472,411 | A | | 12/1995 | Montag et al. |
| 5,472,414 | A | | 12/1995 | Detty |
| 5,700,237 | A | | 12/1997 | Hess |
| 5,718,673 | A | | 2/1998 | Shipstead |
| 5,755,679 | A | | 5/1998 | Selner et al. |
| 5,822,887 | A | * | 10/1998 | Turner ............................ 36/89 |
| 5,921,947 | A | | 7/1999 | Kessler |
| 6,267,742 | B1 | | 7/2001 | Krivosha et al. |
| 6,406,450 | B1 | | 6/2002 | Kowalczyk et al. |
| 6,976,972 | B1 | * | 12/2005 | Bradshaw .................... 602/23 |

* cited by examiner

*Primary Examiner*—Henry Bennett
*Assistant Examiner*—Shumaya B. Ali
(74) *Attorney, Agent, or Firm*—Richard C. Conover

(57) ABSTRACT

A foot and ankle control device including an ankle strap positioned to encircle the leg of a wearer immediately above the ankle. A foot support strap having a medial "D"-ring and a lateral "D"-ring is positioned underneath the wearer's foot adjacent the instep of the foot. A connecting strap is positioned to lie over the arch of the foot and working in cooperation with the foot support strap is used to secure the lateral "D"-ring on the lateral side of the ankle, and the medial "D"-ring on the medial side of the ankle. An elastic lateral control strap is provided for resiliently connecting the lateral "D"-ring to the ankle cuff strap. An elastic medial control strap is also provided for connecting the medial "D"-ring ankle cuff strap.

9 Claims, 6 Drawing Sheets

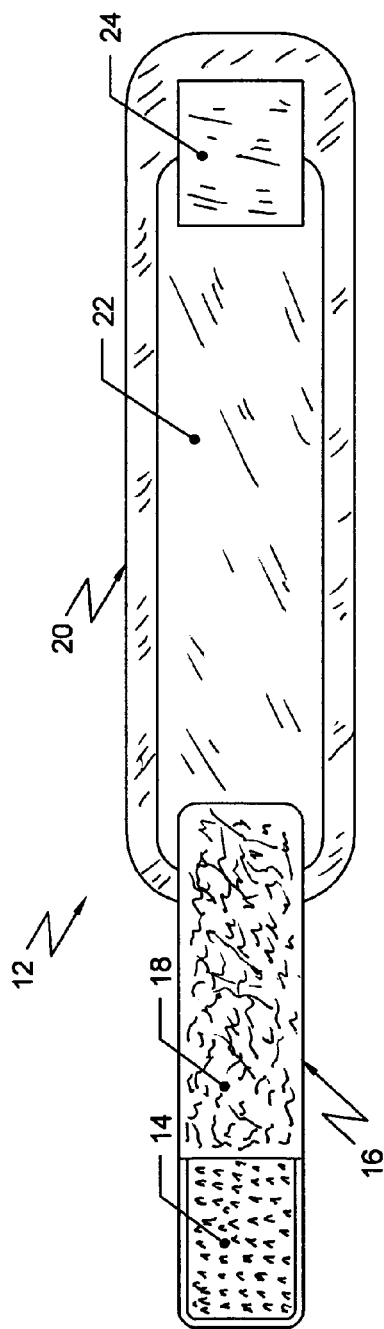
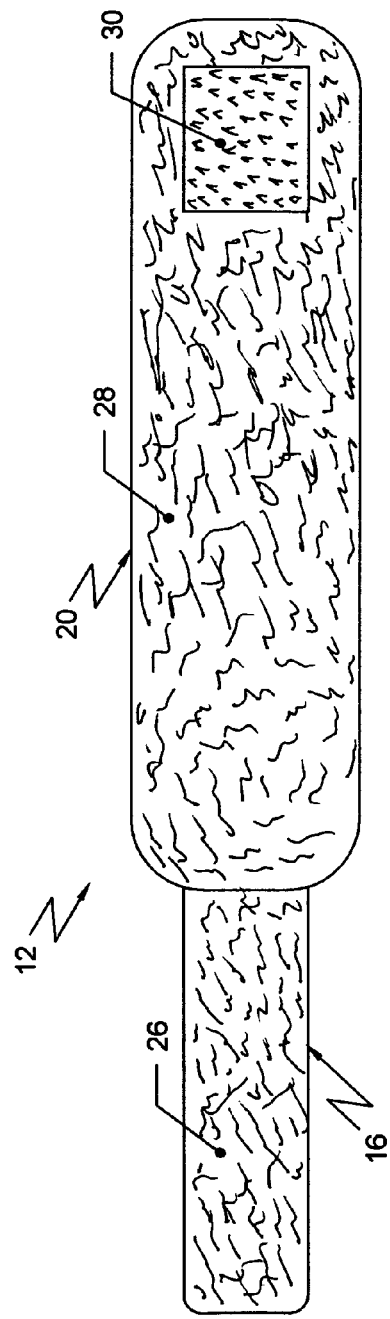
FIG. 2
FIG. 3

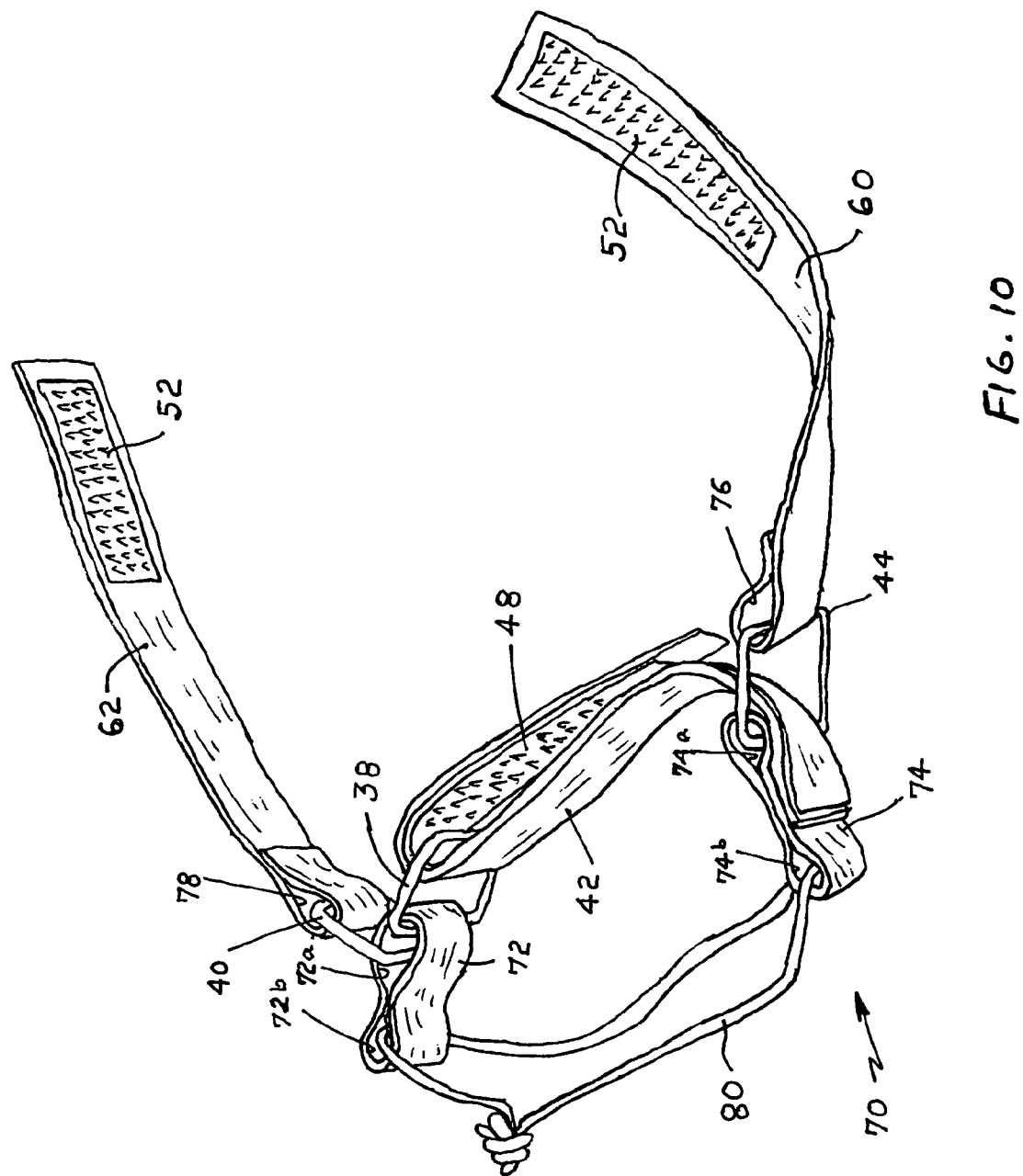

ADJUSTABLE FOOT AND ANKLE DEVICE FOR GAIT CONTROL

This application claims the benefit of provisional application Ser. No. 60/462,413, filed Apr. 10, 2003.

BACKGROUND OF THE INVENTION

The present invention relates to an adjustable foot and ankle device which can be used to control the foot to minimize pronation, supination, toe in and toe out. With this device, the neuromuscular patterning can be changed to correct the gait of a user without resorting to orthotics. The present invention is also used to correct the gait of a user when the user is experiencing pain in the knee, hips, foot or ankle.

SUMMARY OF INVENTION

The foot and ankle control device having an ankle strap positioned to encircle the leg of a wearer immediately above the ankle of the wearer. A foot support strap is provided having a medial "D"-ring attached to the support strap and a lateral "D"-ring attached to the support strap in spaced apart relation with the medial "D"-ring. The foot support strap is positioned underneath the wearer's foot adjacent the instep of the foot. A connecting strap is positioned to lie over the arch of the foot and working in cooperation with the foot support strap is used to secure the lateral "D"-ring on the lateral side of the ankle, and the medial "D"-ring on the medial side of the ankle. An elastic lateral control strap is provided for resiliently connecting the lateral "D"-ring to the ankle cuff strap. An elastic medial control strap is also provided for connecting the medial "D"-ring to the ankle cuff strap.

DESCRIPTION OF THE DRAWINGS

In order that the invention may be clearly understood and readily carried into effect, a preferred embodiment of the invention will now be described, by way of example only, with reference to the accompanying drawings wherein:

FIG. 2 is a top plan view of an ankle cuff strap to be used with the present invention;

FIG. 3 is a bottom plan view of the ankle cuff strap as shown in FIG. 2;

FIG. 10 is a further perspective view of the second embodiment shown in FIG. 9.

DESCRIPTION OF A PREFERRED EMBODIMENT

Figure 1:
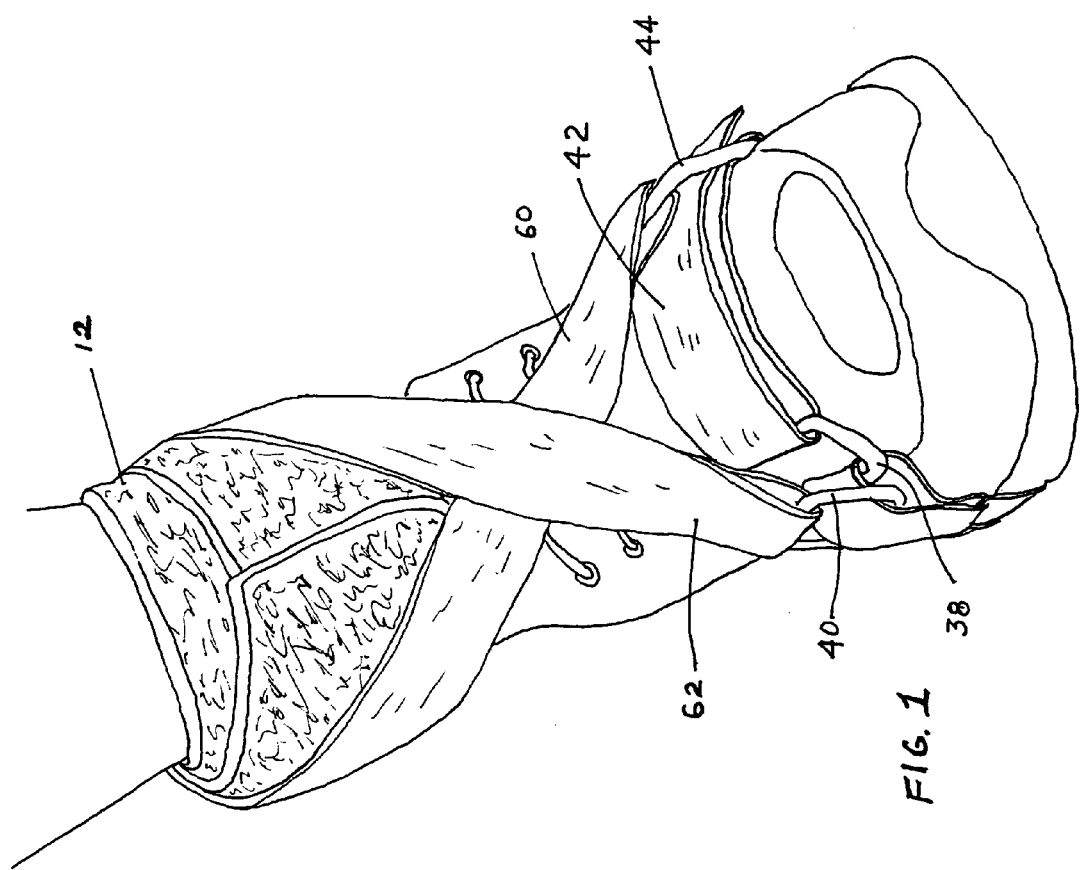
FIG. 1 is a perspective view of a control device according to the present invention installed on the ankle of a wearer.

A foot and ankle control device 10 according to the present invention is shown in FIG. 1 as installed on an ankle of a wearer. The control device 10 includes a ankle cuff strap 12 as shown in FIGS. 2 and 3. As shown in FIG. 2, the cuff strap 12 includes a hook Velcro portion 14 formed on a strap 16. Strap 16 is further provided with a loop Velcro portion 18. The hook Velcro 14 and loop Velcro 18 are secured to strap 16 with stitching. The cuff 12 further includes a body portion 20. A cushioning material 22 is stitched to the body portion 20 and a Velcro backing material 24 is also stitched to the body 20.

As shown in FIG. 3 the bottom side of the cuff 12 has a loop Velcro material 26 stitched to the strap 16. Further, the backside of body 20 has a loop Velcro hook material 28 stitched to the body portion 20. The body 20 is further provided with a hook Velcro portion 30 which is stitched to the body 20. The Velcro backing 24 backs the hook Velcro portion 30.

Figure 4:
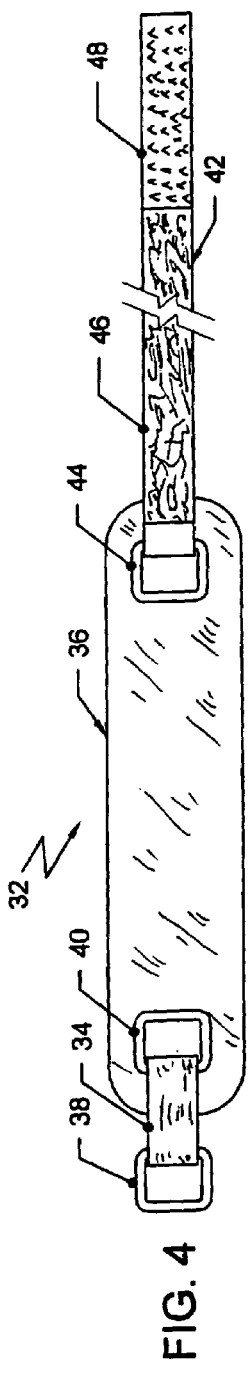
FIG. 4 is a top plan view of a foot support strap used with the present invention.

A foot support strap 32 is shown in FIG. 4. A "D"-ring connecting strap 34 has a middle portion stitched to a main body portion 36 of the foot support strap 32. The strap 34 is looped to secure a "D"-ring 38 at one end of the strap 34. The other end of strap 34 is looped to secure a lateral "D"-ring 40 which is to be positioned on the lateral side of the foot.

Figure 5:
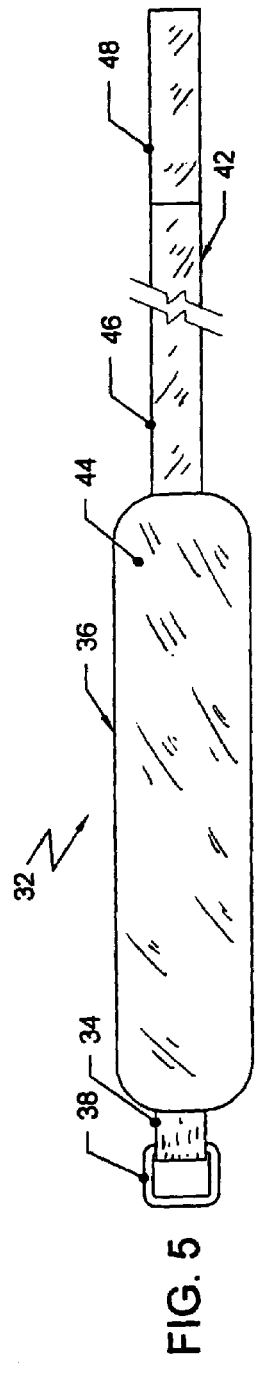
FIG. 5 is a bottom plan view of the support strap shown in FIG. 4.

A connecting strap 42 is sewn to the main body portion 36 at an end of portion 36 opposite the "D"-rings 38 and 40, as shown in FIG. 4. The strap 42 is provided with a looped end which holds a medial "D"-ring 44 which is to be positioned on the medial side of the foot. The side of strap 42 shown in FIG. 4 includes a loop Velcro portion 46 and a hook Velcro portion 48. The reverse side of the foot support strap 32 is shown in FIG. 5.

Figure 6:
FIG. 6 is a top plan view of a control strap used with the present invention.
Figure 7:
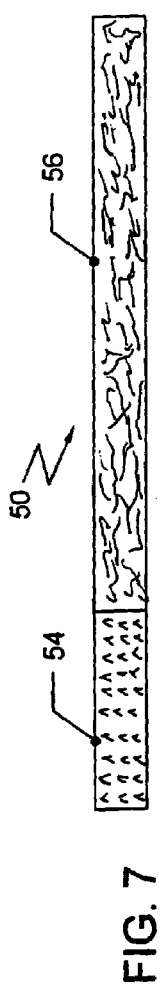
FIG. 7 is a bottom plan view of the control strap as shown in FIG. 6.

FIG. 6 shows a control strap 50 used with the present invention. In a preferred embodiment strap 50 is constructed from elastic material. A top plan view of strap 50 is shown in FIG. 6. A hook Velcro portion 52 is sewn to the control strap 50 as shown in FIG. 6. The back view of strap 50 is shown in FIG. 7. A hook Velcro portion 54 is stitched to control strap 50 as shown. The remainder of strap 50 has a loop Velcro surface also stitched to the control strap 50 as shown in FIG. 7.

In using the invention, the cuff strap 12 is wrapped around the leg of the wearer immediately above the ankle of the wearer, as shown in FIG. 1, with the cushioning surface 22 located adjacent the leg of the user. The hook Velcro 30 is then fastened to the loop Velcro 18 of strap 16. The hook Velcro portion 14 is secured against the loop Velcro portion 28 of the cuff 20.

Next, the foot support strap 32 is positioned with the side, opposite "D"-rings 40 and 42, positioned adjacent the instep of the foot with lateral "D"-ring 40 positioned on the lateral side of the foot and with medial "D"-ring 44 positioned on the medial side of the foot. The strap 42 is then wrapped over the arch of the foot and the free end of the strap 46 inserted through the "D"-ring 38. The strap 42 is then looped back on itself and the hook Velcro portion 48 fastened to the loop Velcro portion 46 of strap 42 to secure the foot support strap 32 to the foot of the user.

Figure 8:
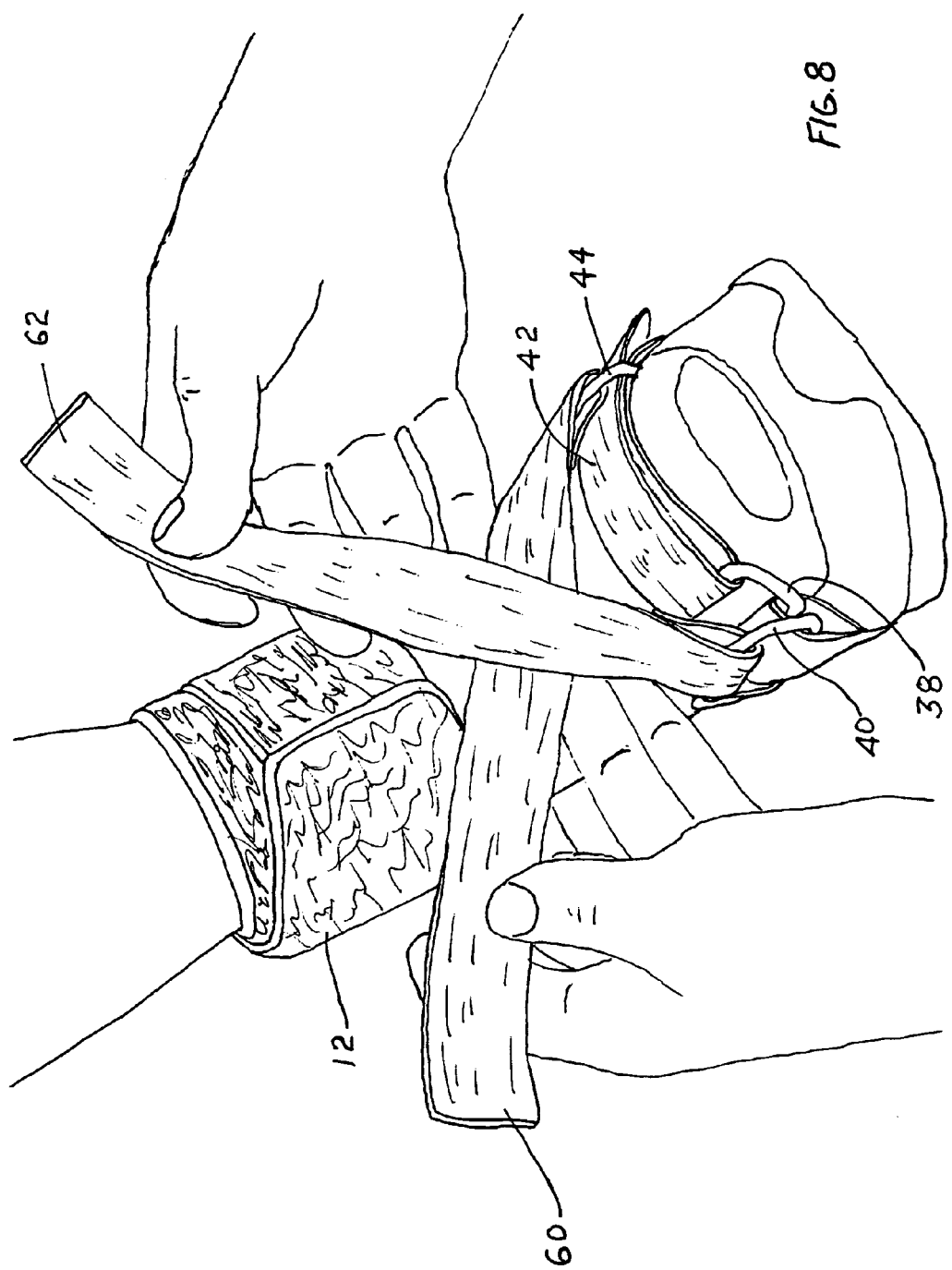
FIG. 8 is a perspective view of a control device according to the present invention being installed on the ankle of a wearer.

In a preferred embodiment, two control straps 50 are used—a medial control strap 60 and a lateral control strap 62, as shown in FIGS. 1 and 8. The end of the medial control strap 60 with the hook Velcro portion 54 is threaded through the medial "D"-ring 44. The medial control strap 60 is then looped on itself and the hook Velcro portion 54 fastened to the loop Velcro portion 56 to secure the medial control strap 60 on the medial "D"-ring 44. Similarly, the lateral control strap 62 is connected to the lateral "D"-ring 40. The free end of the medial control strap 60 is then drawn upwardly and across the arch of the foot to a sufficient extent so that Velcro portion 52 of the medial control strap 60 can be secured to the loop Velcro portion 28 of the cuff strap 12 on the lateral side of the wearer's leg. Similarly, the free end of the lateral control strap 62 is drawn upwardly and across the arch of the foot to a sufficient extent so that the Velcro portion 52 of the lateral control strap 62 can be secured to the loop Velcro portion 28 of the cuff strap 12 on the medial side of the wearer's leg.

Gait control is accomplished with the control device 10 using three different methods. If the analysis of the foot and ankle show that straight dorsiflexion bias is needed, then the medial control strap 60 and the lateral control strap 62 are stretched with equal tension before connecting to the cuff strap 12. If the foot and ankle show that dorsiflexed/pronated bias is needed, then the lateral control strap 62 is stretched to the maximum extent before connecting to the cuff strap 12 and the medial control strap is connected to cuff strap 12 with only moderate tension. If the foot and ankle show that dorsiflex/supinated bias is needed, then the medial control strap 60 is stretched to the maximum extent before connecting the strap to the cuff strap 12. The lateral control strap 62 is connected to cuff strap 12 with only moderate tension.

With the proper tensioning of the medial control strap 60 and the lateral control strap 62, the gait of a wearer can be modified.

Figure 9:
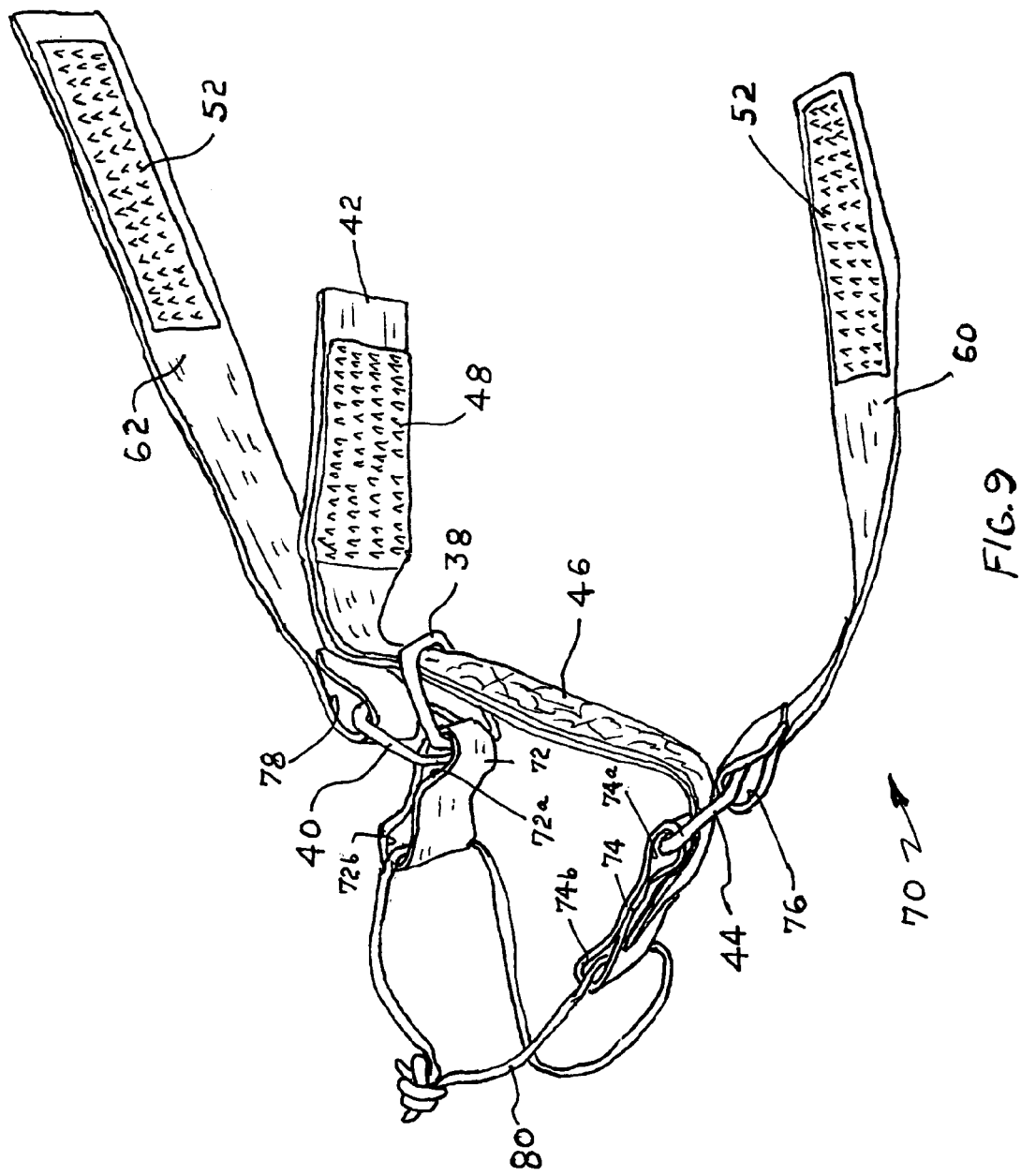
FIG. 9 is a perspective view of a second embodiment of the present invention.

A second embodiment of the present invention is shown in FIGS. 9 and 10. The "D"-ring 38, the lateral "D"-ring 40 and the medial "D"-ring 44 are used in the same manner as the first embodiment. A strap 72 is sewn into a figure "8" configuration and the "D"-rings 38 and 40 are held by loop 72a formed by strap 72. A strap 74 is also sewn into a figure "8" configuration and the "D" ring 44 is held by loop 74a formed in strap 74. A connecting strap 42, similar to the first embodiment, has one end sewn to the strap 74. The strap 42 has a hook Velcro portion 48 and a loop Velcro portion 46, similar to the first embodiment. A medial control strap 60, having a hook Velcro portion 52 has one end sewn into a loop 76 for holding the "D"-ring 44, as shown in FIG. 9. A lateral control strap 62 also has a hook Velcro portion 52 and has one end sewn into a loop 78 for holding the "D"-ring 40, as shown in FIG. 10.

A cord 80 is threaded through loop 72b of strap 72 and also loop 74b of strap 74 and the ends of the cord tied together, as shown in FIGS. 9 and 10.

In using the second embodiment of the present invention, a cuff strap 12 is wrapped around the leg of the wearer immediately above the ankle of the wearer as with the first embodiment. Hook Velcro portion 30 is then fastened to the loop Velcro 18 of strap 16, as shown in FIG. 1. The hook Velcro portion 14 is secured against the loop Velcro portion 28 of the cuff 20.

Next, the cord is positioned underneath the foot adjacent the instep of the foot with the lateral "D"-ring 40 positioned on the lateral side of the foot and with medial "D"-ring 44 positioned on the medial side of the foot. The strap 42 is then wrapped over the arch of the foot and the free end of the strap 42 inserted through the "D"-ring 38. Strap 42 is then looped back on itself and the hook Velcro portion 48 fastened to the loop Velcro portion 46 of strap 42 to secure the cord 80 to the foot of the user. As before, and as shown in FIG. 8, the free end of medial control strap 60 is drawn upwardly across the arch of the foot to a sufficient extent so that hook Velcro portion 52 of the medial control strap 60 can be secured to the loop Velcro portion 28 of the cuff strap 12 on the lateral side of the wearer's leg. Similarly, the free end of the lateral control strap 62 is drawn upwardly across the arch of the foot to a sufficient extent so that the Velcro portion 52 of the lateral control strap 62 can be secured to the loop Velcro portion 28 of the cuff strap 12 on the medial side of the wearer's leg.

Gait control is accomplished in a manner similar to that used with the first embodiment.

While the fundamental novel features of the invention have been shown and described, it should be understood that various substitutions, modifications, and variations may be made by those skilled in the art, without departing from the spirit or scope of the invention. Accordingly, all such modifications or variations are included in the scope of the invention as defined by the following claims:

I claim:

1. Foot and ankle control device comprising:
an ankle cuff strap having two ends;
means for connecting the two ends of the ankle cuff strap together after positioning the ankle cuff strap to encircle a leg of a wearer immediately above an ankle of the wearer;
a foot support strap having a medial "D"-ring attached to the support strap and a lateral "D"-ring attached to the support strap in spaced apart relation with the medial "D"-ring;
the medial "D"-ring positioned at the medial side of the ankle and the lateral "D"-ring positioned at the lateral side of the ankle;
the foot support strap positioned underneath the wearer's foot adjacent the in-step of the foot;
a connecting strap positioned to lie over the arch of the foot and working in cooperation with the foot support strap to secure the lateral "D"-ring on the lateral side of the ankle and the medial "D"-ring on the medial side of the ankle;
an elastic lateral control strap having a first and second ends;
means for connecting the first end of the lateral control strap to the lateral "D"-ring;
means for attaching the second end of the lateral control strap to the ankle cuff strap;
an elastic medial control strap having first and second ends;
means for connecting the first end of the medial control strap to the medial "D"-ring; and
means for connecting the second end of the medial control strap to the ankle cuff strap.

2. The foot and ankle control device according to claim 1 wherein the elastic lateral control strap is positioned to extend from the lateral "D"-ring across the top of the wearer's arch to the medial side of the wearer's leg and the elastic medial control strap is positioned to extend from the medial "D"-ring across the top of the wearer's arch to the lateral side of the wearer's leg.

3. The foot and ankle control device according to claim 1 wherein the means for connecting the two ends of the ankle cuff strap together comprises a hook material and a complimentary loop material.

4. The foot and ankle control device according to claim 1 wherein the means for connecting the lateral control strap to the ankle cuff strap comprises a hook material and a complimentary loop material and wherein the means for connecting the medial control strap to the ankle cuff strap comprises a hook material and a complimentary loop material.

5. Foot and ankle control device comprising:
   an ankle cuff strap having two ends;
   means for connecting the two ends of the ankle cuff strap together after positioning the ankle strap to encircle a leg of a wearer immediately above an ankle of the wearer;
   a foot support strap having first and second ends with a "D"-ring attached to one side of the support strap adjacent the first end and a second "D"-ring attached to the same side of the support strap adjacent the second end;
   the foot support strap positioned underneath the wearer's foot adjacent the instep of the foot with the "D"-rings facing outwardly and with one of the "D"-rings positioned at the medial side of the ankle and the other "D"-ring positioned at the lateral side of the ankle;
   a connecting strap positioned to lie over the arch of the foot and working in cooperation with the foot support strap to secure the lateral "D"-ring on the lateral side of the ankle and the medial "D"-ring on the medial side of the ankle;
   an elastic lateral control strap having first and second ends;
   means for connecting the first end of the lateral control strap to the lateral "D"-ring;
   means for attaching the second end of the lateral control strap to the ankle cuff strap;
   an elastic medial control strap having first and second ends;
   means for connecting the first end of the medial control strap to the medial "D"-ring; and
   means for connecting the second end of the medial control strap to the ankle cuff strap.

6. The foot and ankle control device according to claim 5 wherein the elastic lateral control strap is positioned to extend from the lateral "D"-ring across the top of the wearer's arch to the medial side of the wearer's leg and the elastic medial control strap is positioned to extend from the medial "D"-ring across the top of the wearer's arch to the lateral side of the wearer's leg.

7. The foot and ankle control device according to claim 5 wherein the means for connecting the two ends of the ankle cuff strap together comprises a hook material and a complimentary loop material.

8. The foot and ankle control device according to claim 5 wherein the means for connecting the two ends of the foot support strap together comprises a hook material and a complimentary loop material.

9. The foot and ankle control device according to claim 5 wherein the means for connecting the lateral control strap to the ankle cuff strap comprises a hook material and a complimentary loop material and wherein the means for connecting the medial control strap to the ankle cuff strap comprises a hook material and a complimentary loop material.

* * * * *